(12) United States Patent
Reinauer et al.

(10) Patent No.: US 10,561,452 B2
(45) Date of Patent: Feb. 18, 2020

(54) METHOD FOR MANUFACTURING A PATIENT-SPECIFIC EYE SOCKET COVERING GRID AND PATIENT-SPECIFIC EYE SOCKET COVERING GRID

(71) Applicant: Karl Leibinger Medizintechnik GmbH & Co. KG, Muehlheim (DE)

(72) Inventors: Frank Reinauer, Muehlheim (DE); Oliver Scheunemann, Muehlheim (DE)

(73) Assignee: Karl Leibinger Medizintechnik GmbH & Co., Muehlheim (DE)

(*) Notice: Subject to any disclaimer, the term of this patent is extended or adjusted under 35 U.S.C. 154(b) by 110 days.

(21) Appl. No.: 15/316,728

(22) PCT Filed: Apr. 9, 2015

(86) PCT No.: PCT/EP2015/057745
§ 371 (c)(1),
(2) Date: Dec. 6, 2016

(87) PCT Pub. No.: WO2015/188962
PCT Pub. Date: Dec. 17, 2015

(65) Prior Publication Data
US 2018/0185074 A1 Jul. 5, 2018

(30) Foreign Application Priority Data
Jun. 11, 2014 (EP) .................................. 14172026

(51) Int. Cl.
*A61B 17/80* (2006.01)
*A61F 2/28* (2006.01)
(Continued)

(52) U.S. Cl.
CPC ...... *A61B 17/8061* (2013.01); *A61B 17/8057* (2013.01); *A61B 17/8085* (2013.01);
(Continued)

(58) Field of Classification Search
CPC ............ A61F 2/2875; A61F 2002/2878; A61F 2002/30617; A61F 2/30942;
(Continued)

(56) References Cited

U.S. PATENT DOCUMENTS

| | | |
|---|---|---|
| 5,139,497 A | 8/1992 | Tilghman |
| 5,383,931 A | 1/1995 | Hehli |

(Continued)

FOREIGN PATENT DOCUMENTS

| | | |
|---|---|---|
| CN | 101637414 A | 2/2010 |
| CN | 102292051 A | 12/2011 |

(Continued)

OTHER PUBLICATIONS

Written Opinion of PCT/EP2015/057745 dated Jun. 15, 2015.
Office Action, CN 2015800309022, dated Jul. 13, 2018 (pp. 4).
CN Search Report, CN 201580030922, dated Jul. 3, 2018 (3 pp.).

*Primary Examiner* — Samuel S Hanna
(74) *Attorney, Agent, or Firm* — Eversheds Sutherland (US) LLP

(57) ABSTRACT

The present application relates to an eye socket covering grid that includes a curved main body with an external closing edge, a lower side which, in the implanted state, is facing the bone or bones forming the eye socket, and an upper side distant from the lower side, wherein at least one optically identifiable linear channel for representing at least one insertion vector is formed on the upper side. The application also relates to a method for producing such an eye socket covering grid, in particular an eye socket covering grid adapted in a patient-specific manner.

5 Claims, 5 Drawing Sheets

(51) Int. Cl.
*A61B 17/56* (2006.01)
*A61B 90/00* (2016.01)
*A61F 2/30* (2006.01)
*A61B 17/00* (2006.01)

(52) U.S. Cl.
CPC .. *A61F 2/2875* (2013.01); *A61B 2017/00526* (2013.01); *A61B 2017/568* (2013.01); *A61B 2090/0807* (2016.02); *A61F 2/30942* (2013.01); *A61F 2002/2878* (2013.01); *A61F 2002/30112* (2013.01); *A61F 2002/30617* (2013.01)

(58) Field of Classification Search
CPC .......... A61B 2017/568; A61B 17/8061; A61B 17/8085; A61B 2090/0807
See application file for complete search history.

(56) References Cited

U.S. PATENT DOCUMENTS

| | | |
|---|---|---|
| 5,743,913 A | 4/1998 | Wellisz |
| 6,071,291 A | 6/2000 | Forst |
| 7,662,155 B2 * | 2/2010 | Metzger ............. A61B 17/8061 606/280 |
| 2003/0109784 A1 | 6/2003 | Loh |
| 2011/0082559 A1 | 4/2011 | Hartdegen et al. |
| 2011/0319745 A1 | 12/2011 | Frey |
| 2012/0010711 A1 | 1/2012 | Antonyshyn |
| 2012/0165878 A1 | 6/2012 | Hwa et al. |
| 2013/0135312 A1 | 5/2013 | Yang et al. |

FOREIGN PATENT DOCUMENTS

| | | | |
|---|---|---|---|
| CN | 103002831 A | 3/2013 | |
| CN | 103096819 A | 5/2013 | |
| CN | 203619652 U | 6/2014 | |
| CN | 203619658 U | 6/2014 | |
| DE | 19746396 A1 | 10/1997 | |
| EP | 1965735 B1 | 2/2009 | |
| EP | 2030596 | 3/2009 | |
| EP | 2923676 A1 * | 9/2015 | ........... A61F 2/2875 |
| WO | 2008063494 A2 | 5/2008 | |

* cited by examiner

METHOD FOR MANUFACTURING A PATIENT-SPECIFIC EYE SOCKET COVERING GRID AND PATIENT-SPECIFIC EYE SOCKET COVERING GRID

TECHNICAL FIELD

The invention relates to a patient-specific eye socket covering grid to all four eye socket walls, in particular in the manner of a three-dimensional orbital mesh which comprises a main body that is curved/bent in an S-shape/curved in several places, with an external closing edge/surround that is normally peripheral, whereby the main body has a lower side which, in the implanted state, is facing the bone or bones forming the eye socket and the main body has an upper side distant from the lower side.

The invention also relates to a method for producing such an eye socket covering grid for all four eye socket walls which is adapted in a patient-specific manner. It has the capacity to be linked to any defects in the midface.

Under the grid, an arrangement of longitudinal parts is subsumed at regular or irregular intervals. It can exhibit a surface structure which is net-like in configuration.

BACKGROUND OF THE INVENTION

Eye socket covering grids are known from the state of the art, such as EP 1 965 735 B1 for example. Here an implant is deployed for use as a replacement for an orbital floor. The implant is configured as an eye socket covering grid and therefore rests on the orbital floor. Such an implant, like a mesh or grid, can also be used for lateral orbital wall reconstruction. It can also be inserted in a self-supporting manner and does not necessarily have to rest on the floor. In the publication mentioned, an implant is presented for use as a replacement of an eye socket base and optionally also of a medial and lateral eye socket wall in the form of a single-section pre-formed plate comprising a first section, a second section and a third section, whereby the first section is formed corresponding to an eye socket base and the second section is formed corresponding to a medial side wall, and the first section and the second section are adjoined along a first predetermined line, whereby the third section is arranged for the attachment of the implant to the front eye socket edge, whereby particular emphasis is given to the fact that the first predefined line is defined in the publication mentioned as a breakage line along which a doctor can easily remove one segment.

Plates in grid-like configuration are also known in similar form for use in other parts of the body.

For example, DE 197 46 396 A1 discloses a grid for fixing bone parts or for bridging bone faults. Such a grid can also be used on the skull. Ultimately this German publication proposes a grid for use in the skull and jaw area that is made of biocompatible materials with a net-like structure and with recesses to hold bone screws by means of which the grid can be fixed to the bone. The ribs form meandering, continuous, periodical series of ribs along the main axis of the grid.

When attached to the bone, the eye socket covering grid, i.e. the device designed to come into contact with the orbital floor, may not obstruct the eyeball support. The eyeball support is not spherical, however, but extends longitudinally, in particular in an S-shape fashion.

The eye socket covering grids known from the state of the art are unfortunately often too large, not adapted to the individual cranial bones requiring treatment and/or defective and frequently also difficult to adapt.

SUMMARY OF THE INVENTION

The purpose of the invention is to offer a remedy here and provide the operating surgeon with an initial patient-specific structure of an eye socket covering grid which is as optimum as possible, in particular an eye socket covering grid that is not too large and is pre-fitted to the defect requiring treatment and simple in terms of its capacity for detailed adaptation. What is more, a method is to be presented which enables the simple manufacture of such an eye socket covering grid. Finally, a method will also be presented for carrying out permanent treatment of injuries to the orbital floor and lateral orbital walls in a fast and precise manner, with the option of establishing a link with the midface structures which also require replacement, for example—for instance in the case of extended tumour-related resection defects.

This object is achieved according to the invention by means of a generic eye socket covering grid which on the upper side comprises at least one optically identifiable channel for representing at least one insertion vector.

This allows the eye socket covering grid to be positioned on or in the patient more simply and more precisely. The patient can be a mammal, in particular a human being or another mammalian animal. The eye socket covering grid is to be placed between a soft tissue filling the eye socket and the bone structure which forms the eye socket proper. The eye socket covering grid is then an implant which rests on the bone structure, being at least in contact with three points if possible and covered by soft tissue after implantation. Of course it is also possible to use less than three resting points. If the eye socket covering grid is configured according to the invention, the insertion is more precise, atraumatic and injury-free/injury-freer; in particular, position monitoring in X-ray-based imaging processes is capable of objectification. The eye socket covering grid's patient compatibility is significantly improved. Wear comfort is increased.

Preferred embodiments of the invention are claimed in the dependent claims and are explained below in more detail.

For example, it is especially advantageous if the channel provides a linear connection between two points, in other words it is configured in linear fashion at least in sections, or is preferably entirely linear in configuration.

It is advantageous if the main body is configured as a rib-forming, perforated component. This improves adaptability to the body of a human being, for example. What is more, the risk of forming a closed space is reduced, i.e. in the event of secondary bleeding the grid openings allow blood to run out into neighbouring paranasal sinuses.

If ribs are arranged in such a way in the main body that continuous, longitudinal slits run through the surface stretched through the main body, in particular extending from the lower side to the upper side of the main body, the compatibility of the eye socket covering grid in the patient is improved, thereby reducing weight, saving material, reducing costs and making it possible to create a drainage system.

It is also expedient if the slits are oriented (almost) orthogonally to the closing edge/surround and/or are distributed so as to be equidistant from each other. This makes the insertion process easier to control. Other advantages such as the preservation of a particularly rigid implant can also come into effect.

If the channel has two channel walls which protrude from the upper side and run equally spaced from one other, a control instrument can easily be placed on the channel and perform a controlling function during insertion. The raised configuration of the channel walls effectively prevents the control instrument from moving outside the channel.

Structural weakness is avoided if the channel exhibits a channel base between the channel walls which is formed by the upper side of the main body or at least runs through the space formed by the upper surface. Manufacture can also be carried out in a low-cost manner in this case.

It is also advantageous if the channel, preferably designed to be interrupted/continuously or sectionally interrupted, runs from a front edge, which is nearest to an operating surgeon, to a peak area, which in the implanted state is nearest or near to an optic nerve/optic channel. Placing the peak area onto the bone is simplified, avoiding irritation or damage to the optic nerve/optic channel. It is also easier to bring the peak area into contact with a bone section which is deeply embedded in soft tissue. Here it is advantageous if the implant is additionally over-bent in the peak area so as to preserve a greater distance from the optic nerve.

The insertion process can be performed even more precisely if a second channel is available to represent an additional insertion vector. The second channel is then configured in a similar or identical way to the first channel and provides the transition between the orbital floor and the side wall.

In particular, the first channel can be oriented so as to run obliquely to the second channel, especially so as to be at an angular offset by an angle a in the range of 20° to 40°, in particular 22.5°.

If the channel edges form a guide for a control instrument which is inserted between them and pushed along them, any slipping of the control instrument is efficiently avoided.

In order for the insertion of the eye socket covering grid/the implant to be able to be interrupted in sections and/or controlled, it is advantageous if between the channel walls and/or on/in the channel base a navigation stop in the form of a prominence or a recess is available/configured which can preferably be identified in a haptic or tactile manner by the control instrument, and preferably several navigation stops are configured per channel, whereby there are the same number or different numbers of navigation stops per channel, for example one navigation stop fewer in the second channel than in the first channel. Navigation stops can be placed on the entire body of the implant, but preferably on the channel. The navigations stops are defined as landmarks which act as an intraoperative guide. Furthermore, it is possible to realise a trajectory plan which incorporates the recessed insertion vectors and allows them to be followed.

It is also advantageous if the first channel is oriented parallel to a sagittal level of the patient undergoing treatment and/or the second channel or the first channel are oriented parallel to a transverse sagittal level of the patient undergoing treatment. A three-dimensionally flowing insertion movement is then easier for the operating surgeon to control in terms of its precision.

If the peak area has a different curve from most of the main body, in particular as compared to the directly adjacent/neighbouring area of the main body, preferably exhibiting a convex arch, i.e. increasingly curved/extending in the direction of the bone, for example, this facilitates injury-free handling of the eye socket grid when implanting it in the body of a human being, for example.

It is expedient if the first channel and the second channel meet or almost meet in the peak area. Of course it is possible for the intersection point of the two channels to be outside the implant, for example approx. 1 mm to approx. 4 mm, in particular approx. 1.3 mm outside the closing edge of the eye socket grid.

One advantageous embodiment is also characterized in that a length scale is applied which is representative of the measurements on the main body.

A further configuration is characterized in that the symbols that are relevant for the length scale, such as numbers, are applied next to one of the channels, for example to the right or left of the first or second channel, on/in the upper side, preferably in the manner of a (calibrated) ruler. In particular, this allows the distance from the peak area to be marked. It is then simple to mark gaps of approx. 15 mm, approx. 25 mm and approx. 35 mm as well as interim values such as approx. 10 mm, approx. 20 mm and/or approx. 30 mm. The markings can be set at intervals of 5 mm. In order to improve adaptation to the patient, it is advantageous if the front edge exhibits a convex curvature on the upper side and/or a concave curvature on the lower side. This also enables grasping to be facilitated for the operating surgeon. In particular, it makes it easier for the operating surgeon to use their fingers to hold the eye socket grid manually at the edge.

The attachment of the eye socket grid to the bone is more precise if there is in the front edge at least one clearance hole to receive a screw attaching the eye socket grid to the bone, preferably several clearance holes for several screws and/or the clearance hole is oriented across the upper and/or lower side of the main body (in the region of the clearance hole) so as to follow a bore vector. This also effectively prevents the eye socket grid from slipping relative to the bone. It has proven effective to calculate a screw vector in the clearance hole so as to know in advance where most bone is available and to be able to make effective use of it.

It is advantageous if a tear passage area is physically predefined/configured.

It is also advantageous if the main body is formed as a plate, net and/or multi-layered component.

If the continuous slits or perforations are designed as a closing system, patient compatibility of the eye socket grid is improved, in particular in order to create a drainage facility in the event of potential secondary bleeding.

An advantageous embodiment is also characterized in that the closing edge is made of out thicker material than (most of) the rest of the main body, in the manner of a cord with atraumatic effect.

It has also proven advantageous in terms of compatibility if the eye socket grid is prepared and/or adapted for a specific patient.

If the continuous slits are arranged in such a way that unintentional folding over of partial areas of the main body is more difficult or impossible, this creates or makes it possible to create a highly resilient/rigid implant. In particular, it is advantageous if a medial wall is designed to be only as high as required by the specific patient but as high as possible if necessary.

Patient compatibility is improved if the peak area is designed in the manner of a snow shovel in reverse so as to be curved away from the optic nerve.

The invention also relates to a method for producing an eye socket covering grid that is adapted in a patient-specific manner. This allows an eye socket covering grid according to the invention to be made. Individual stages are performed according to the invention which should preferably be carried out in sequence. In one stage, a (3D) primary model is created of the eye socket bone structure to be covered or replaced in a (human or animal) patient requiring treatment. A subsequent stage concerns the establishment of a limit area representative of the maximum spatial extension of the planned eye socket covering grid, at least in terms of its two-dimensional extension. Another stage concerns the transfer of a (2D) secondary model onto the (3D) primary model, for example within a predefined/random limit area, in such a way that the geometrical constitution of the primary model is transposed onto the initial form of the original secondary model so as to result in a (3D) tertiary model. After these stages, manufacture of the eye socket covering grid is carried out on the basis of the data after a separation stage from the original (3D) primary model, i.e. based on the (3D) tertiary model. In essence, therefore, a 2D template is virtually projected onto a base, whereby the base can exhibit elevations replicated in a patient-specific manner or replicating patient-specific features.

Preferred embodiments of the method are also claimed in the dependent claims and are explained in more detail below.

It is advantageous if the primary model is a 3D model and/or the secondary model is a 2D model and/or the tertiary model is a 3D model.

It is expedient if generative techniques are used for manufacturing such as sintering processes, and/or CNC, milling and/or injection moulding processes. Laser sintering techniques such as SLM, i.e. Selective Laser Melting, have proven particularly effective. Here it is advantageous if the eye socket grid is made of only one or several metal materials or only of plastic or a mixture of metal and plastic. Ceramic components can also be added. It is also possible for the eye socket grid to be made entirely of ceramic. Zirconium oxide and hydroxylapatite are also suitable options.

It is also expedient if the secondary model is structured/composed of several layers.

An advantageous embodiment is also characterized in that, when transferring or planning/designing the primary or secondary model, a deliberate deviation from the 3D patient data is accepted/applied so as to optimise the edge of the eye socket grid for the specific operating surgeon in question and/or the implantation procedure.

If the peak area of the eye socket grid is prepared for contact with the bone, for example curved or more strongly curved than specified by the 3D patient data, and/or the front edge of the eye socket grid is prepared as a grip area for the (manual) grasp of the operating surgeon, for example curved or more strongly curved than specified by the 3D patient data, this enables an eye socket grid to be created that can be especially securely handled.

It is advantageous if the perforations or continuous slits are deliberately planned/elaborated in an orthogonal manner in relation to a patient-specific vector which is appropriate/applicable for the insertion/implantation procedure, for example an insertion vector.

Especially good coordination can be achieved if a cord on the closing edge exhibits a thickness of approx. 0.3 to approx. 0.7 mm, e.g. approx. 0.5 mm and the surface of the main body inside this exhibits a thickness of approx. 0.1 mm to approx. 0.5 mm, for example 0.3 mm. These figures are approximate figures and can be subject to a deviation of 10% or 20%.

This also applies to a cord which is configured to be between approx. 0.1 mm to approx. 0.3 mm thicker, for example 0.2 mm thicker than the load-bearing surface of the main body.

It is advantageous if an internal matrix is specifically/freely chosen in relation to several factors concerning structure, geometry, pore size and biomechanical properties, for example in terms of adaptation/imitation/improvement of the material to be replaced/supplemented in the relevant anatomical region of the patient.

It is also advantageous if a patient-specific identification is applied to the eye socket grid, for example in the manner of a barcode and/or a character sequence consisting of letters and/or numbers, for example during the manufacturing stage and using the material of which the eye socket grid is made, preferably in a (laser) sintering process, as an elevation, in particular to reproduce the patient's name and/or the implantation position/location.

BRIEF DESCRIPTION OF THE DRAWING

The invention is also explained in more detail below by means of drawings FIGS. 1 to 5.

It should be noted that the individual features described in the dependent claims of the device can be combined with the generic features, without the feature that at least one optically identifiable linear channel is marked on the upper side for representing at least one insertion vector. The method according to the invention also concerns the manufacture of such an eye socket covering grid.

It is also possible to install/implant several eye socket covering grids on top of one another. The individually combined and at least partially overlapping eye socket covering grids can also each exhibit different shapes. For example it is possible to give preference to a cylindrical or a triangular shape.

DETAILED DESCRIPTION

Figure 1:
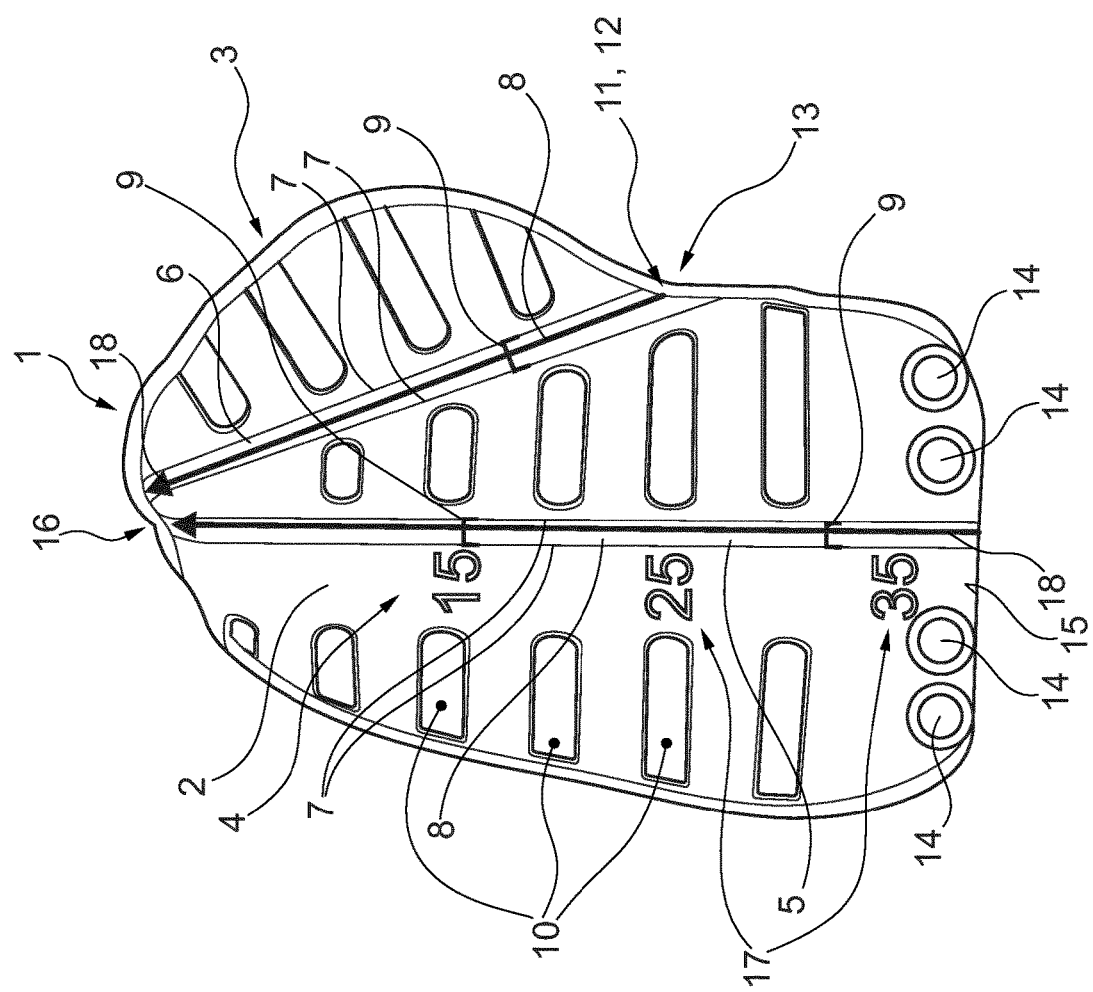
FIG. 1 shows a top view of an eye socket covering grid according to the invention.

FIG. 1 shows a first embodiment of an eye socket covering grid 1 according to the invention. The eye socket covering grid is configured as an orbital mesh. It exhibits a main body 2 that is curved/bent/arched at multiple points.

The main body 2 comprises on its outer side an essentially peripheral/self-contained outer closing edge/surround 3. A lower side of the eye socket covering grid 1, in particular of the main body 2 and the closing edge/surround 3, is configured in a patient-specific manner. As such the inner and outer structure is patient-specific. In terms of bending stiffness and/or elastic modulus, the interior matrix of the main body and the material used, for example a titanium alloy, is selected so that it is adapted to the adjacent patient-specific anatomical region, if possible precisely replicating it.

In this way, the eye socket covering grid 1 can be specifically adapted to the bone or bones forming the eye socket.

The upper side of the implant/eye socket covering grid 1 is to be provided with a reference mark 4. A first channel 5 and a second channel 6 are configured on this upper side 4. Both channels 5 and 6 run in a linear fashion and are identifiable optically and in a tactile manner. Each channel 5 and 6 defines an insertion vector. Each channel 5 and 6 exhibits two channel walls 7 which protrude orthogonally from the upper side 4, whereby a channel base 8 is defined between the two channel walls 7 of a channel 5 and 6 respectively.

There is a navigation stop 9 in/against/on the channel base 8. In the first channel 5, two navigation stops 9 are provided, while in the second channel 6 only a single navigation stop 9 is provided.

In the main body 2, perforations or slits/continuous slits 10 are provided in the manner of through-openings. They are longitudinal in shape. They each run orthogonally to the closing edge/surround 3 formed by a cord 11, which exhibits an almost circular, elliptical or rounded cross section. For this reason, the cord is atraumatic in effect.

There is also an anatomical boundary 12. A precise tear passage area 13 is likewise physically configured and predefined.

Four through-holes 14 are provided in a front edge 15 of the eye socket covering grid 1. The through-holes 14 define a bore vector or follow a predefined bore vector. The bore vector is specific to an operating surgeon. The bore vector runs obliquely to the upper side 4 and/or the lower side of the main body 2 of the eye socket covering grid 1. In the through-holes 14 it is possible to insert screws which can be anchored in the bone.

A peak area 16 is at the opposite end of the main body 2. Here, the insertion vectors meet inside or outside the material forming the main body 2.

A length scale 17 is configured by numbers such as the FIGS. 15, 25 and 35 on the left-hand side of the first channel 5, following this/starting from the peak area 16. The length scale 17 is configured in the manner of a (calibrated) ruler.

The slits/continuous slits 10 form a drainage system. In the peak area 16, a critical area is predefined in terms of the optic channel/optic nerve. The insertion vector underlying channels 5 and 6 bears the reference numeral 18.

The channels 5 and 6 are not only advantageous for the implantation procedure, i.e. when inserting the eye socket covering grid 1, but also in terms of the subsequent monitoring of the implantation procedure. In this way it is possible to enable quality assurance of the procedure without injuring the patient. At any time it is possible to compare the actual position of the eye socket covering grid 1 with a desired position on the computer. This facilitates postoperative monitoring of the position. It is possible to achieve correspondence with the 3D data set as was planned. For this purpose, the patient can be provided with a reference point which is fed into the computer. It is particular suitable to use three reference points. The channels 5 and 6 then act as a guidance line with interim points/recesses. The guidance line is thus the first channel 5 or the second channel 6 and the interim points/recesses are the navigation stops 9. The channels 5 and 6 thus form a physical double contour/line for the improved guidance of a control instrument.

The peak area 16 can be configured in the manner of a reversed snow shovel, in other words forming curve that protrudes away from the optic nerve so that any spiking of the eye muscle or mechanical irritation/perforation of the optic nerve is ruled out/avoided. Perforations such as the slits/continuous slits 10 are deliberately oriented orthogonally to a patient-specific vector, in particular the insertion vector 18. The peak area 16 is prepared for abutment against the bone. The edge, in particular formed by the closing edge/surround 3, can be planned in such a way that the implant forms a protrusion which can be abutted against the bone and/or provides a handle for the operating surgeon.

It should be noted that after the manufacture of the eye socket covering grid 1, a sterilization stage can and should be carried out.

While up to now so-called "average implants" have been created, i.e. not configured in a patient-specific manner, it is now possible to configure them in a patient-specific manner. For this purpose, a secondary model can be placed on a primary model, similar to placing a linen cloth on a rake. The secondary model can be a conglomerate of varying layers and shapes. It is desirable to separate the implant from the 3D model. The implant can then be a model, for example in the form of a standardized 3D data set, for example in the form of an STL data set. The secondary model can be a BMP template, whereby JPEG, TIFF and similar formats are possible. Absorbable material can of course also be used as material for the eye socket covering grid 1.

Figure 2:
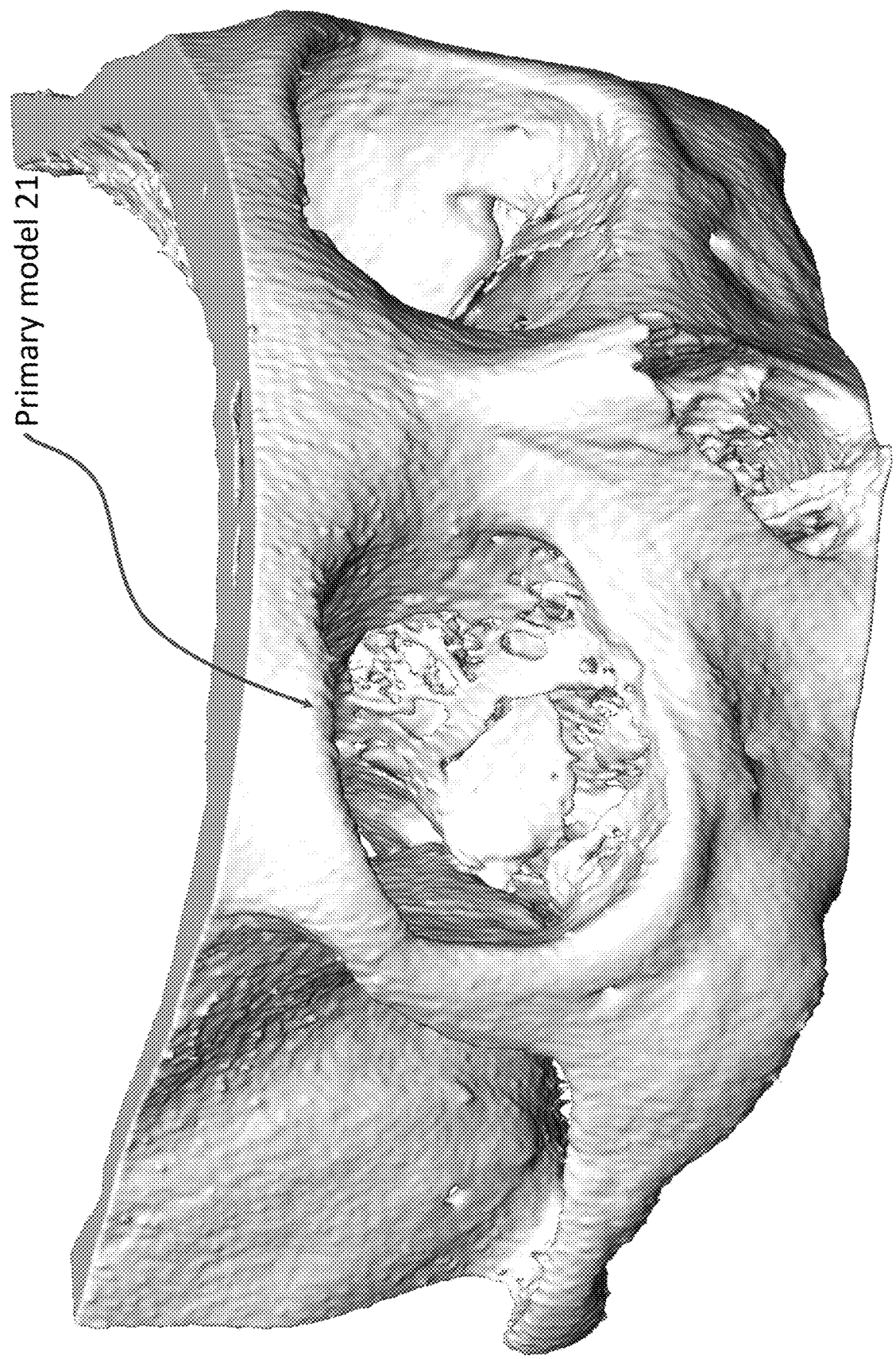
FIG. 2 shows an example of the (3D) primary model according to the invention.
Figure 3:
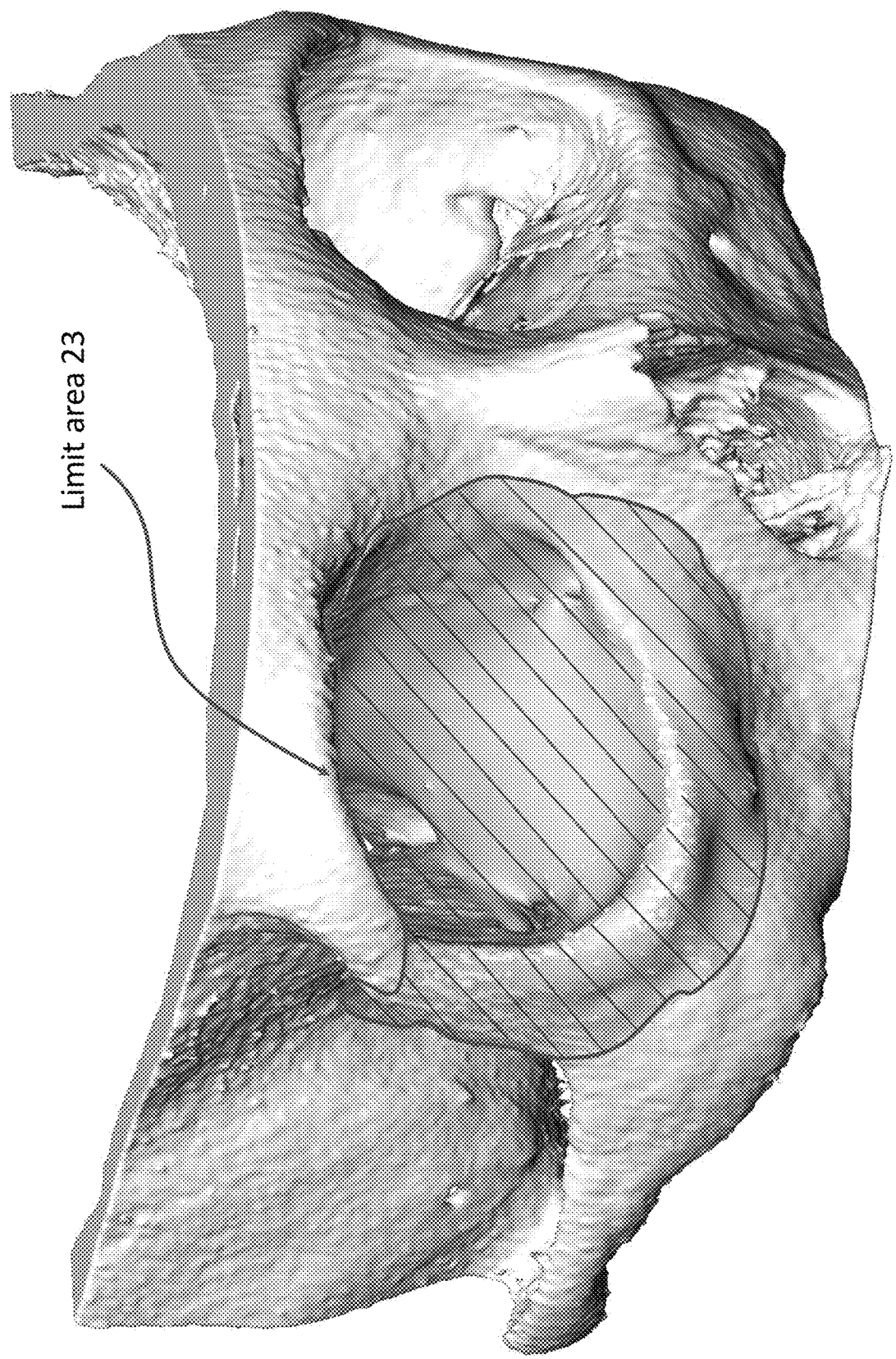
FIG. 3 shows an example of the limit area according to the invention.
Figure 4:
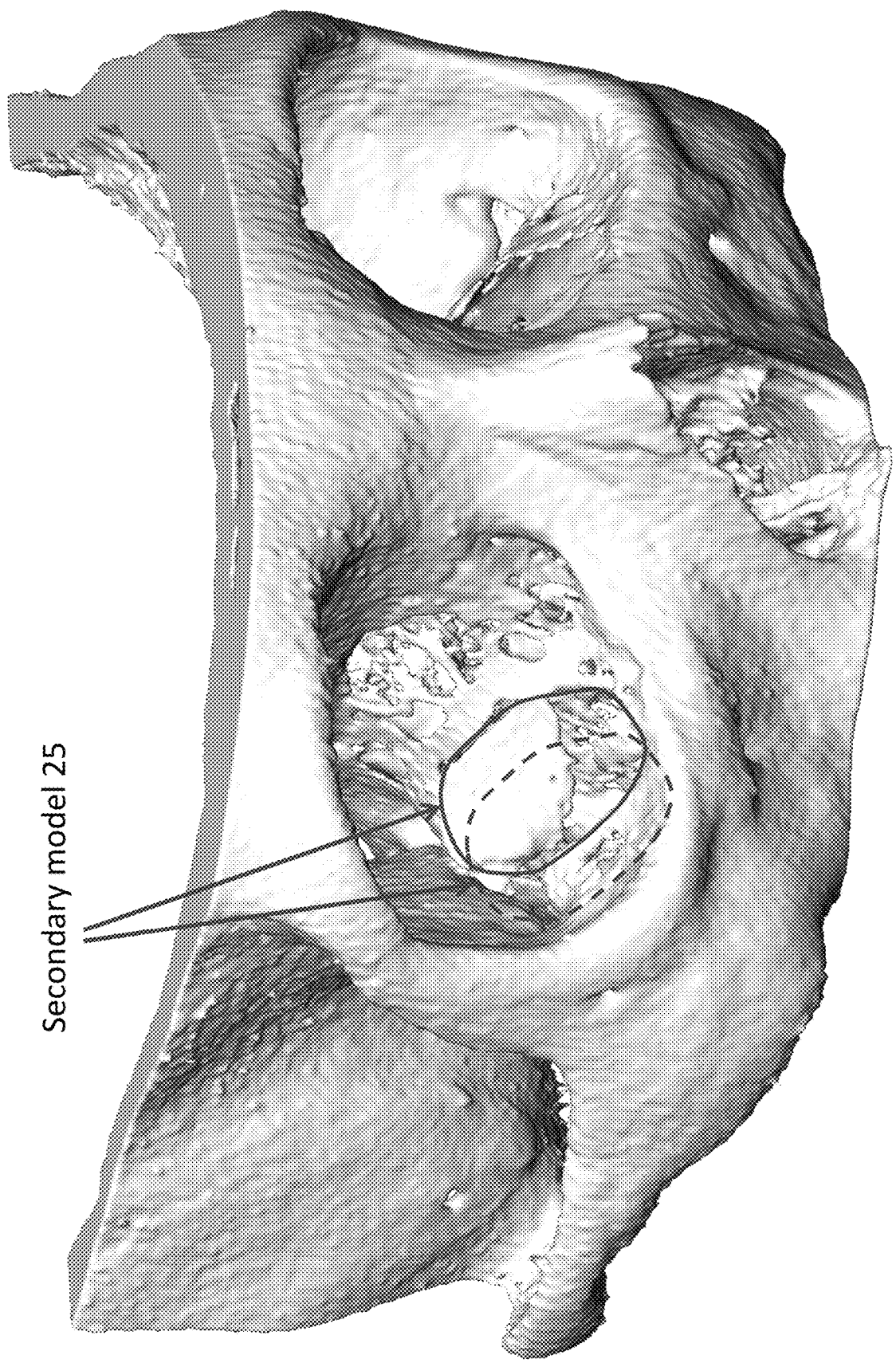
FIG. 4 shows an example of the (2D) secondary model with layers according to the invention.
Figure 5:
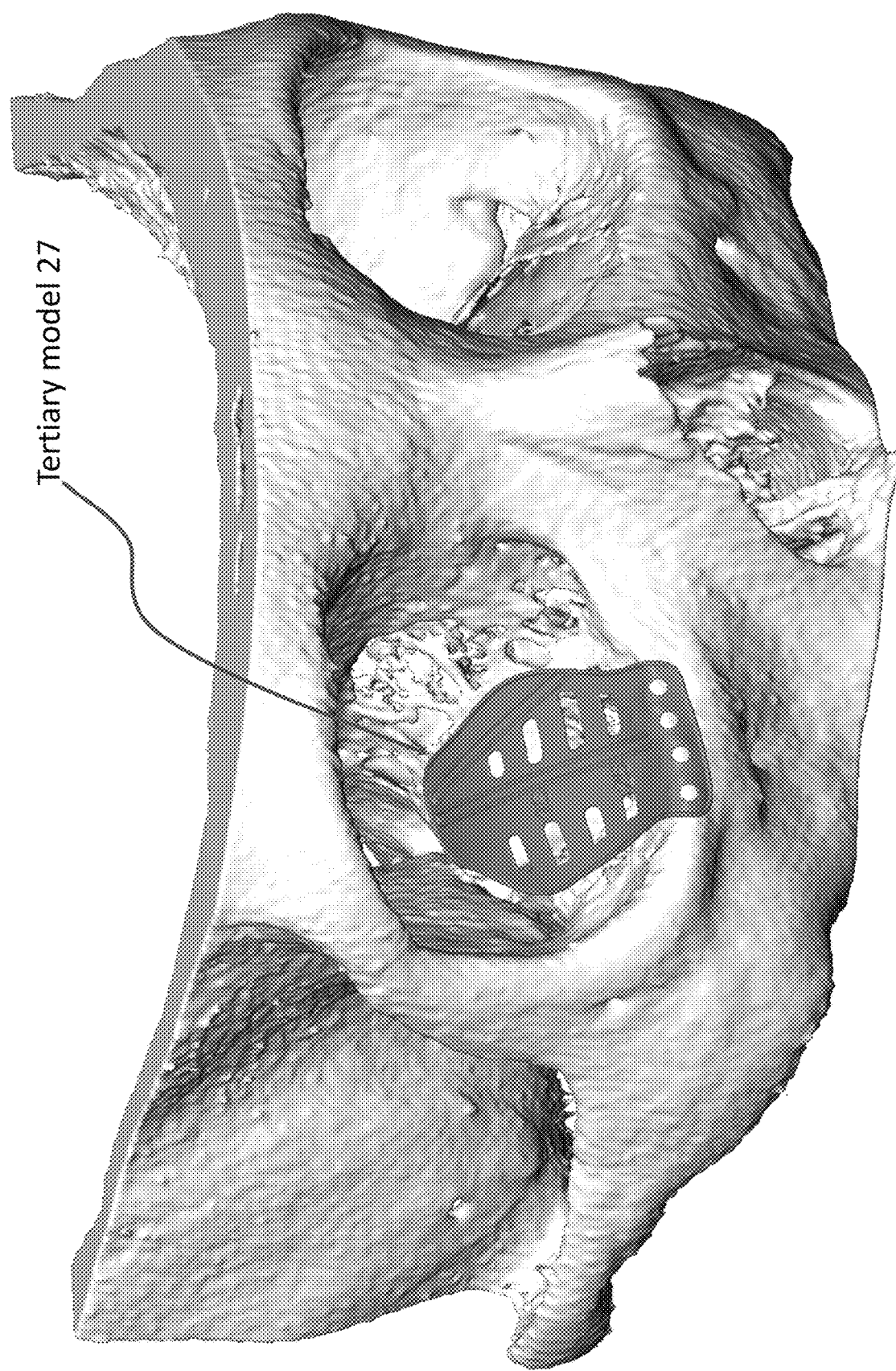
FIG. 5 shows an example of the (3D) tertiary model according to the invention. The figures are diagrammatic in nature only and serves solely to explain the invention.

FIG. 2 shows a flow chart with exemplary method steps described herein for manufacturing an eye socket covering grid 1 adapted in a patient-specific manner. At step 20, a primary model 21 is created of a bone structure in the area of an eye socket of a patient requiring treatment. After which at step 22, a limit area 23 is established which is representative of a maximum spatial extension of the eye socket covering grid 1. After which at step 24, a secondary model 25 is transferred onto the primary model 21. At step 26, the secondary model 25 is transferred in such a way that the geometrical constitution of the primary model 21 is transposed onto an initial form of the original secondary model 25 so as to result in a tertiary model 27. At step 28, on the data of the tertiary model 27, the manufacture of the eye socket covering grid 1 is based after a separation stage from the primary model 21.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

LIST OF REFERENCE NUMERALS

1 Eye socket covering grid
2 Main body
3 Closing edge/surround
4 Upper side
5 First channel
6 Second channel
7 Channel wall
8 Channel base
9 Navigation stop
10 Slit/continuous slit
11 Cord/smooth border
12 Anatomical boundary
13 Tear passage area
14 Through-hole
15 Front edge
16 Peak area
17 Length scale
18 Insertion vector
20 step
21 primary model
22 step
23 limited area
24 step 25 secondary model
26 step
27 tertiary model
28 step

We claim:

1. A method for manufacturing an eye socket covering grid, said eye socket covering grid comprising a curved main body with an external closing edge, and the main body has a lower side which, in an implanted state, is facing a bone or bones forming an eye socket and the main body has an upper side distant from the lower side, wherein at least one optically identifiable linear channel for representing at least one insertion vector is formed on the upper side, adapted in a patient-specific manner, whereby, a primary model is created of a bone structure in the area of the eye socket of a patient requiring treatment by a computer based on an image captured by an imaging device, after which a limit area is established by the computer which is representative of a maximum spatial extension of the eye socket covering grid, after which a secondary model is transferred onto the primary model by the computer in such a way that a geometrical constitution of the primary model is transposed onto an initial form of the original secondary model so as to result in a tertiary model, separating the tertiary model data from the primary model, and manufacturing the eye socket covering grid based on the tertiary model data via generative techniques.

2. The method according to claim 1, characterized in that the primary model is a 3D model and/or the secondary model is a 2D model and/or the tertiary model is a 3D model.

3. The method according to claim 1, characterized in that generative techniques are used for manufacturing such as sintering processes, and/or CNC, milling or injection moulding processes.

4. The method according to claim 1, characterized in that the eye socket covering grid is made of only one or several metal materials or only of plastic or a mixture of metal and plastic.

5. The method according to claim 1, characterized in that the secondary model is structured/composed of several layers.

* * * * *